(12) United States Patent
Incavo

(10) Patent No.: US 6,267,015 B1
(45) Date of Patent: Jul. 31, 2001

(54) SAMPLING DEVICE FOR CONDENSABLE GASES

(75) Inventor: Joseph Alan Incavo, Uniontown, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/466,251

(22) Filed: Dec. 17, 1999

(51) Int. Cl.⁷ .................................................. G01N 1/14
(52) U.S. Cl. ..................................... 73/863.11; 73/863.84
(58) Field of Search ................................. 73/23.41, 23.42, 73/863.11, 863.12, 864.21, 864.35, 863.84, 864.74, 864.86, 864.87; 250/258; 422/100

(56) References Cited

U.S. PATENT DOCUMENTS

| | | |
|---|---|---|
| 5,287,758 * | 2/1994 | Geiss et al. ......................... 73/863.11 |
| 6,114,178 * | 9/2000 | Dezael et al. ....................... 73/863.11 |
| 6,116,098 * | 9/2000 | Lubek et al. ........................ 73/863.11 |

* cited by examiner

Primary Examiner—Robert Raevis
(74) Attorney, Agent, or Firm—David E Wheeler

(57) ABSTRACT

An apparatus and method for sampling gases at elevated temperatures which is amenable to analysis in a manufacturing environment is described. In particular the method and apparatus can be used to determine accurate compositions of gas mixtures contained in blisters of elastomeric products. The device comprises a syringe 15,15a and a heated block 12,12a for receiving and holding syringe 15,15a, and for preheating or maintaining the temperature of syringe 15,15a. A thermostat may be associated with heating block 12,12a for controlling its temperature close to the temperature of a product from which a gas sample is taken. In a method of the invention, the syringe 15,15a is preheated to a temperature equal to or greater than the temperature of a sample which is to be obtained, the valve 24 is opened, the needle is used to penetrate a cavity where the sample resides, the valve 24 is closed, and the syringe is placed in heating block 12,12a where the temperature is substantially maintained until the sample gas can be analyzed.

3 Claims, 2 Drawing Sheets

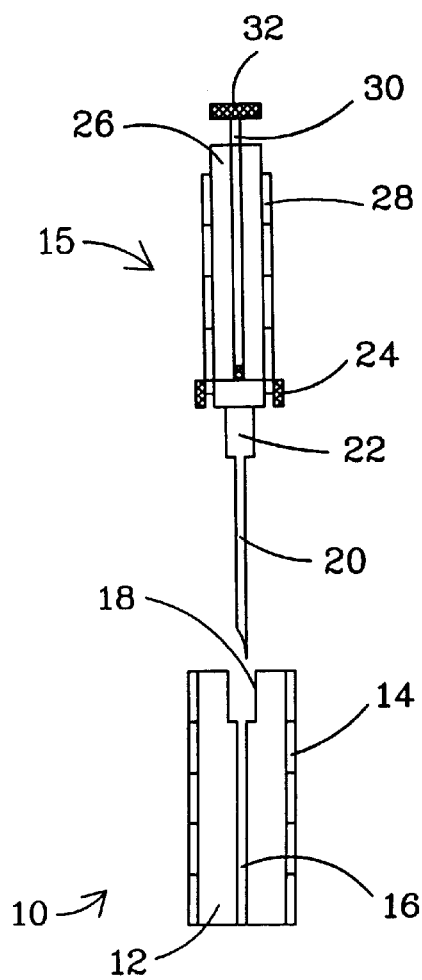
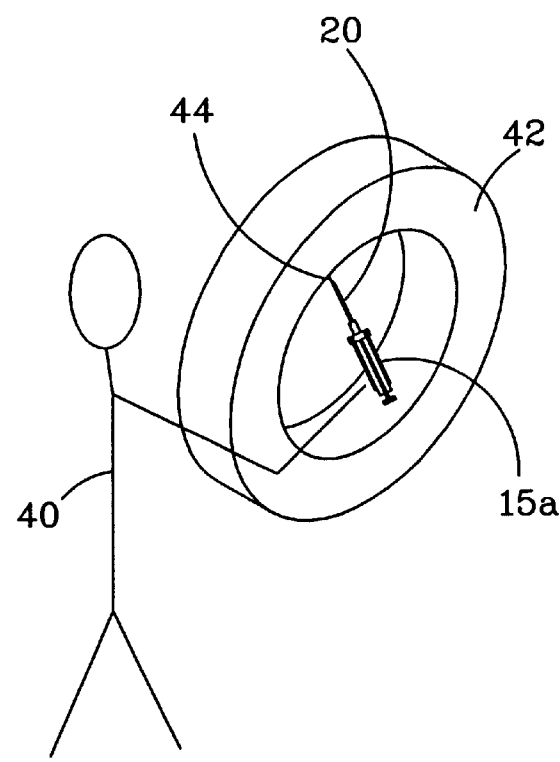
Fig 1
Fig 3

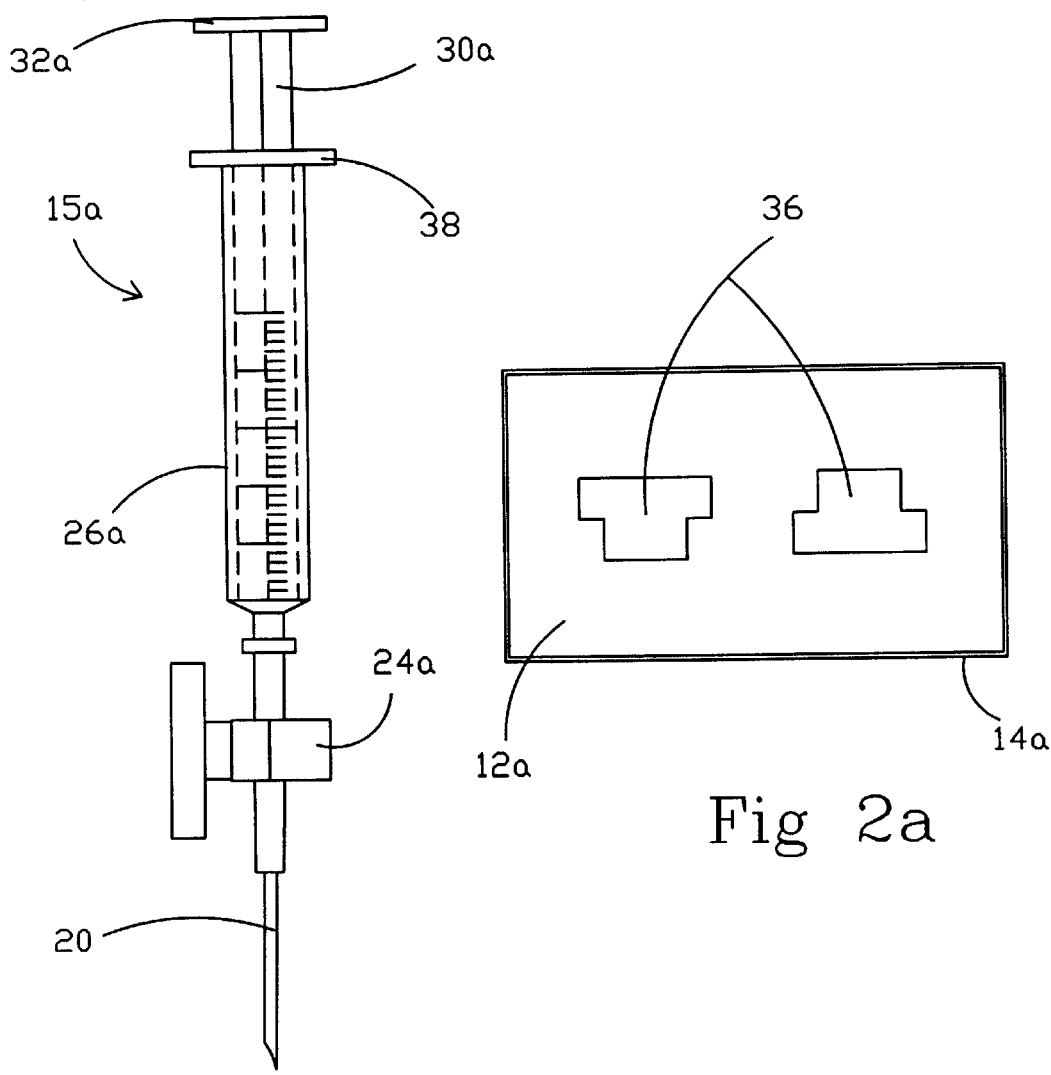
Fig 2a
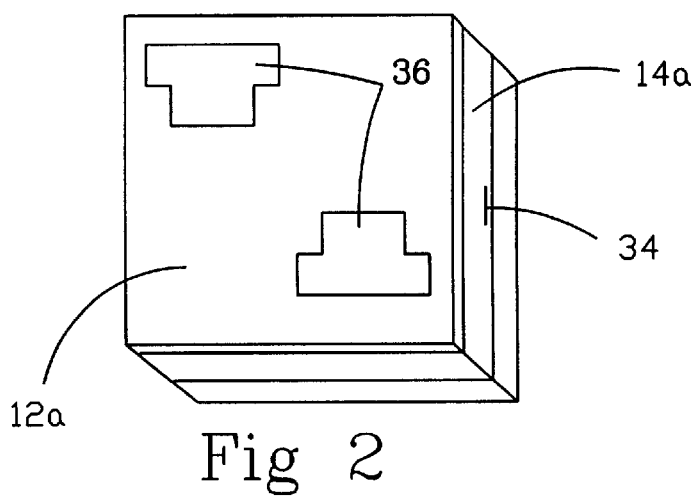
Fig 2
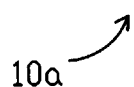

SAMPLING DEVICE FOR CONDENSABLE GASES

TECHNICAL FIELD

The invention relates to an apparatus and a method for obtaining gas samples at elevated temperatures.

BACKGROUND OF THE INVENTION

The obtaining of gas samples at elevated temperatures can be useful in monitoring chemical processes, gas phase compositions and the like. One possible use of the method and apparatus of the invention is to analyze gases that cause blisters in elastomeric products.

The composition of a gas that causes a blister in an elastomeric product may provide clues as to the source of the gas. Knowing the composition of the gases contained in the blister, one skilled in the art may be able to identify their source and eliminate the blistering.

Blisters are usually found when an elastomeric product is heated, such as in a curing process. If the blister gas is not sampled within minutes of its formation, cooling of the elastomeric article can cause major changes in the gas composition due to condensation, absorption, leaking, and possibly chemical reactions.

It is not practical or economical to place analysis equipment such as mass spectrometers, gas chromatographs, etc., on the factory floor so that a technician can obtain a sample of gas from an elastomeric product immediately after it is removed from a mold, and inject the gas directly into gas analyzing equipment. Accordingly, the gas sample must be obtained, removed from the factory floor, and then subjected to analysis. If the gas is permitted to cool while being transported from the factory floor to the laboratory, the compositional information needed by the analyst to solve the blistering problem could well be lost.

It is an object of this invention to provide a method and an apparatus whereby a gas sample can be maintained substantially in the condition, including the same composition and temperature, that the sample was in when it was obtained.

Other objects of the invention will be apparent from the following description and claims.

SUMMARY OF THE INVENTION

An apparatus for sampling gases at elevated temperatures comprises (a) a gas tight syringe comprising a barrel having an inside and an outside, a plunger inside the barrel and extending from a first end thereof, (b) a hollow needle attached to a second end of the barrel, the hollow needle communicating with the inside of the barrel, (c) heat insulating means surrounding the barrel of the syringe, and (d) a heated block adapted to receive the syringe, wherein the heated block is surrounded by insulating means. In the illustrated embodiment, the heat insulating means has heating elements which are used to heat the barrel of the syringe. The insulating means is also used to heat the heating block.

A method of the invention, for obtaining gas samples at elevated temperatures, comprises the steps of (a) preheating a gas tight syringe, the syringe comprising a barrel having a plunger within the barrel and extending from first end thereof, and a hollow needle which is in communication with the inside of the barrel attached to a second end thereof, to a temperature of within ±10° C. of the expected temperature of a sample, (b) inserting the needle into gases which are to be sampled and analyzed, (c) withdrawing the plunger in the barrel a specified distance to obtain a specific size sample of gases, and (d) removing the needle from the gases.

In the illustrated embodiment, the method comprises the further step of placing a syringe containing a sample in a heating block to maintain the temperature of the sample. In addition, the method may comprise the further steps of (e) preheating the syringe and the sample to a temperature substantially equivalent to the temperature at which the sample is obtained, and (f) analyzing the sample.

In a specific embodiment, the method is used to sample gases which cause a blister during curing of a pneumatic tire, and the step (b) of inserting the needle into gases to be analyzed comprises the further step of penetrating the blister with the needle, and the further step of delivering a specific quantity of sample gases from the syringe into analyzing equipment selected from the group consisting of a gas chromatograph, a mass spectrometer, an infrared analyzer (IR), a gas analyzer, and combinations thereof.

BRIEF DESCRIPTION OF THE DRAWINGS

FIG. 1 illustrates an embodiment of the invention wherein the apparatus comprises an insulated syringe and an insulated block.

FIGS. 2 and 2a illustrate a second embodiment comprising a syringe made of a single material, and a heating block capable of receiving and retaining the entire syringe.

FIG. 3 illustrates how a syringe may be used in the method of the invention for obtaining a sample gas.

DETAILED DESCRIPTION OF THE INVENTION

In the illustrated embodiment of the invention, it is described herein how a portable device may be used to sample gases from a blister in an elastomeric product while the product is still warm. Other uses of the invention will be apparent to those skilled in the art.

With reference now to FIG. 1, the apparatus 10 of the invention comprises a syringe 15 having a needle 20, and a metal block 12 having a hole 16 drilled therein for receipt of needle 20. Block 12 is preferably made of a heat conductive material, and in the illustrated embodiment, block 12 comprises aluminum. Surrounding block 12 is heating tape 14, which not only insulates the block but contains heating wires therein which can be used to maintain the block at an elevated temperature.

Syringe 15 comprises the needle 20, the needle holder 22 which connects needle 20 to barrel 26, and plunger 30 which fits tightly within barrel 26. Plunger 30 has a finger grip 32 which can be used to provide leverage when the plunger 30 is pushed into or removed from barrel 26. The syringe has a valve 24 which can be used to close off or open a passageway from barrel 26 to needle 20. Syringe 15 is also wrapped by insulating tape 28 which insulates barrel 26 and contains heating wires which may be used to maintain barrel 26 at an elevated temperature.

In the illustrated embodiment, syringe 15 has a glass barrel 26, a plastic valve 24, which may be polypropylene, polyvinylchloride, Teflon®, or nylon, for example, and a metal needle holder 22. In the use of this embodiment, it has been found that the different materials used in the construction of syringe 15 expand at different rates, and the different rates of expansion may cause leaks. Accordingly, although this embodiment is useful in the invention, the temperature range in which it can be used is limited. It has been found experimentally that good results are obtained, for samples that are collected using syringe 15, up to 90° C.

With reference now to FIGS. 2 and 2a, in a second embodiment of the invention, an apparatus 10a comprises a metal block 12a which is machined to provide cavities 36 which can be used to receive a syringe 15a up to its collar 38. Block 12a is wrapped by insulating tape 14a which contains heating wires which may be used to maintain block 12a at an elevated temperature. A thermostat 34 is included in tape 14a, which can be used to control the temperature of block 12a. Block 12a is also preferably aluminum.

Other materials that can be used to make block 12,12a include any grade of steel, copper or brass.

Syringe 15a has a needle 20, a valve 24a which fits into cavity 36, a barrel 26a, and a plunger 30a. All parts of syringe 15a, including collar 38 and finger grip 32a, and excepting needle 20, are made of the same material. Since all components of syringe 15a are made of the same material, the coefficient of expansion of all parts of the syringe is the same, and all parts of the syringe expand or contract at the same rate when the syringe is heated.

Syringe 15a may be made of any suitable material which has suitable expansion properties and is sufficiently resistant to heat for the intended purposes. Examples of such materials are nylon, polyethylene, polypropylene, polyvinylchloride, polyaryletherketones, and fluorinated polymers. In the illustrated embodiment, syringe 15a is made of polypropylene.

The polypropylene provides a high degree of inertness to reactive organics, and the low cost makes practical disposal of the syringe after one use, thus eliminating the possibility of analyte carryover. Tests at syringe temperature of 115° C. for air/water mixtures of relative humidities of 10–90% at 21° C. indicate that moisture is not absorbed on the surface of the syringe. Tests under these conditions also indicate that plasticizer leaching does not occur.

In the illustrated embodiment, the metal needle is permanently fixed to the lure-lock adapter on the syringe by a thermoset epoxy.

In the use of syringe 15a, it has been found that barrel 26a can be deformed slightly as plunger 30a is moved in and out of barrel 26a, and accordingly a very tight fit having a very tight seal can be made between barrel 26a and plunger 30a. Polypropylene softens at 140° C., and can be used safely up to a temperature of about 130° C.

With reference now to FIG. 3, the method of the invention is illustrated for use in obtaining a sample of blister gas from an elastomeric tire 42. In the method of the invention, a lab analyst 40 checks the temperature of an elastomeric article and adjusts the temperature of heating block 12,12a be greater than or equal to the maximum temperature of the article.

In the illustrated embodiment, when the temperature of heating block 12,12a stabilizes, lab analyst 40 removes a preheated syringe 15,15a from heating block 12,12a, where it rests preferably with valve 24, 24a open, and closes valve 24,24a, and uses the needle 20 of syringe 15,15a to penetrate a blister 44, opens valve 24, 24a and by grabbing finger grip 32,32a and pulling back on plunger 30,30a, creates a vacuum in barrel 26a, causing the blister gas to enter barrel 26a through opened valve 24,24a. After the sample is pulled into syringe 15,15a, lab analyst 40 then closes valve 24,24a to trap the gases inside barrel 26,26a. The analyst then places syringe 15,15a into heating block 12,12a. When syringe 15a is used, it is placed in one of the cavities 36 in heating block 12a, and the syringe is inserted into cavity 36 up to collar 38 of the syringe.

The syringe 15,15a is permitted to rest in heating block 12,12a, substantially at the same temperature at which the sample was obtained, until the analyst is able to subject the gas sample to analysis.

The invention is further illustrated with reference to the following example.

EXAMPLE

In this example, the sampling technique of the invention is compared with a prior art sampling technique.

Table 1 shows the results of samples tested using the apparatus of the invention, compared to the prior art technique of warming a syringe in an oven and walking it over to a gas chromatograph (GC).

TABLE 1

Sampling of Saturated Hexane Vapor at 50.0° C.

| Sampling Technique | Measured Concentration m/m % | % Actual |
|---|---|---|
| Conventional Oven | | |
| 30 sec transfer to GC | 50.5 | 95% |
| 60 sec transfer to GC | 53.3 | 100% |
| Current Method | 78.9 | 148% |
| a | 52.3 | 98% |
| b | 58.0 | 109% |
| c | 53.3 | 100% |
| d | 54.8 | 103% |
| e | 57.4 | 108% |
| | | mean: 103% |

The data shows that using the method of the invention, there is an 11% differential between five samples, whereas using the prior art techniques, there is a 53% differential between four samples that are handled for different periods of time. It is noted for the samples of the invention, there is only a small lag time between removing a syringe from a heating block, and injecting a sample into analysis equipment.

In Table 2, changes in the composition caused by letting the sample cool are illustrated.

TABLE 2

Sampling Hot Tire Blisters

| | Blister 1 | | Blister 2 | |
|---|---|---|---|---|
| | Hot | Cold | Hot | Cold |
| Air | 95.0% | 99.2% | 93.0% | 99.2% |
| Component 1 | 5.0% | 0.80% | 5.0% | 0.70% |
| Component 2 | | | 2.0% | 0.1% |

Table 2 shows that when the temperature of the gas is maintained (hot analysis), there is less air and more component of the blister gas detected than when the sample is allowed to cool. In two blisters sampled, the percentage of air increases, and the percentage of non-air components decreases by more than 20% in each case.

While the invention has been specifically illustrated and described, those skilled in the art will recognize that the invention may be variously modified and practiced without departing from the spirit of the invention. The invention is limited only by the following claims.

What is claimed is:

1. A method for obtaining gas samples from a blister in a pneumatic tire at elevated temperatures comprising the steps of (a) preheating a gas tight syringe, said syringe comprising a barrel, a plunger within said barrel and extending from a first end thereof, and a hollow needle which is in communication with the inside of said barrel attached to a second end thereof, in a heating block to a temperature of within ±10° C. of the expected temperature of a sample (b) penetrating said blister with said needle and inserting the needle into gases which are to be sampled and analyzed (c) withdrawing said plunger from said barrel a specified distance to obtain a specific size sample of gases, (d) removing said needle from said gases, and (e) placing a syringe containing a sample in a heating block to maintain the temperature of said sample for analysis.

2. The method of claim 1 comprising the further steps of (e) preheating said syringe and said sample to a temperature substantially equivalent to the temperature at which the sample was obtained, and (f) analyzing said sample.

3. The method of claim 1 comprising the further step of delivering a specific quantity of sample gases from said syringe into analyzing equipment selected from the group consisting of a gas chromatograph, a mass spectrometer, an infrared analyzer (IR), a gas analyzer, and combinations thereof.

* * * * *